(12) United States Patent
Amorese et al.

(10) Patent No.: US 10,927,405 B2
(45) Date of Patent: Feb. 23, 2021

(54) MOLECULAR TAG ATTACHMENT AND TRANSFER

(71) Applicant: NuGEN Technologies, Inc., San Carlos, CA (US)

(72) Inventors: Douglas A. Amorese, Los Altos, CA (US); Stephanie C. Huelga, Belmont, CA (US); Bin Li, San Carlos, CA (US)

(73) Assignee: NUGEN TECHNOLOGIES, INC., Redwood City, CA (US)

( * ) Notice: Subject to any disclaimer, the term of this patent is extended or adjusted under 35 U.S.C. 154(b) by 103 days.

(21) Appl. No.: 16/245,600

(22) Filed: Jan. 11, 2019

(65) Prior Publication Data

US 2019/0144928 A1     May 16, 2019

Related U.S. Application Data

(62) Division of application No. 15/294,132, filed on Oct. 14, 2016, now Pat. No. 10,190,155.

(51) Int. Cl.
    *C12Q 1/6827*     (2018.01)
    *C12Q 1/6806*     (2018.01)

(52) U.S. Cl.
    CPC ......... *C12Q 1/6827* (2013.01); *C12Q 1/6806* (2013.01)

(58) Field of Classification Search
    CPC .......................... C12Q 1/6827; C12Q 1/6806
    See application file for complete search history.

(56) References Cited

U.S. PATENT DOCUMENTS

| | | |
|---|---|---|
| 5,384,242 A | 1/1995 | Oakes |
| 5,750,341 A | 5/1998 | Macevicz |
| 5,969,119 A | 10/1999 | Macevicz |
| 6,110,709 A | 8/2000 | Ausubel et al. |
| 6,225,109 B1 | 5/2001 | Juncosa et al. |
| 6,251,639 B1 | 6/2001 | Kurn |
| 6,287,766 B1 | 9/2001 | Nolan et al. |
| 6,306,597 B1 | 10/2001 | Macevicz |
| 6,449,562 B1 | 9/2002 | Chandler et al. |
| 7,170,050 B2 | 1/2007 | Turner et al. |
| 7,211,390 B2 | 5/2007 | Rothberg et al. |
| 7,244,559 B2 | 7/2007 | Rothberg et al. |
| 7,244,567 B2 | 7/2007 | Chen et al. |
| 7,264,929 B2 | 9/2007 | Rothberg et al. |

(Continued)

FOREIGN PATENT DOCUMENTS

| | | |
|---|---|---|
| WO | 2008/093098 A2 | 8/2008 |
| WO | 2012/061832 A1 | 5/2012 |

(Continued)

OTHER PUBLICATIONS

Benson, 2013, Genbank, Nucl Acids Res 41:D36-D42.

(Continued)

*Primary Examiner* — Joseph G. Dauner
(74) *Attorney, Agent, or Firm* — Brown Rudnick LLP; Thomas C. Meyers

(57) ABSTRACT

Described herein are methods, compositions and kits for identifying modifications that could lead to false positive detections in nucleic acid sequencing. In some embodiments, the methods, compositions and kits provided herein are useful for reducing potential of false positive detection of variants caused by errors during sample preparation or sequencing.

24 Claims, 3 Drawing Sheets

(56) References Cited

U.S. PATENT DOCUMENTS

| | | |
|---|---|---|
| 7,276,720 B2 | 10/2007 | Ulmer |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,361,468 B2 | 4/2008 | Liu et al. |
| 7,405,281 B2 | 7/2008 | Xu et al. |
| 7,414,117 B2 | 8/2008 | Saito et al. |
| 7,462,452 B2 | 12/2008 | Williams et al. |
| 7,462,468 B1 | 12/2008 | Williams et al. |
| 7,476,503 B2 | 1/2009 | Turner et al. |
| 7,476,504 B2 | 1/2009 | Turner |
| 7,491,498 B2 | 2/2009 | Lapidus et al. |
| 7,501,245 B2 | 3/2009 | Quake et al. |
| 2005/0130173 A1* | 6/2005 | Leamon ............ G01N 21/6452 506/2 |
| 2005/0202490 A1* | 9/2005 | Makarov ............ C12N 15/1072 435/6.12 |
| 2006/0024678 A1 | 2/2006 | Buzby |
| 2006/0024711 A1 | 2/2006 | Lapidus et al. |
| 2006/0040297 A1* | 2/2006 | Leamon ............ C12N 15/1075 435/6.18 |
| 2006/0286566 A1 | 12/2006 | Lapidus et al. |
| 2007/0172839 A1* | 7/2007 | Smith ................ C12N 15/1093 435/6.12 |
| 2008/0087826 A1 | 4/2008 | Harris et al. |
| 2008/0103058 A1 | 5/2008 | Siddiqi |
| 2008/0206764 A1 | 8/2008 | Williams et al. |
| 2008/0213770 A1 | 9/2008 | Williams et al. |
| 2009/0024331 A1 | 1/2009 | Tomaney et al. |
| 2009/0026082 A1 | 1/2009 | Rothberg et al. |
| 2009/0029385 A1 | 1/2009 | Christians et al. |
| 2009/0061439 A1 | 3/2009 | Buzby |
| 2009/0068655 A1 | 3/2009 | Williams |
| 2009/0081737 A1* | 3/2009 | Brenner .................. C12P 19/34 435/91.1 |
| 2009/0233802 A1 | 9/2009 | Bignell et al. |
| 2009/0269749 A1* | 10/2009 | Van Eijk ............ C12Q 1/6874 435/6.11 |
| 2010/0311602 A1* | 12/2010 | Levy .................... C12Q 1/6869 506/9 |
| 2011/0319290 A1* | 12/2011 | Raymond ............ C12Q 1/6855 506/9 |
| 2012/0015821 A1* | 1/2012 | Raymond ................ C40B 40/08 506/2 |
| 2012/0071331 A1 | 3/2012 | Casbon et al. |
| 2012/0208705 A1 | 8/2012 | Steemers et al. |
| 2012/0220494 A1 | 8/2012 | Samuels et al. |
| 2013/0231253 A1 | 9/2013 | Amorese et al. |
| 2015/0299767 A1* | 10/2015 | Armour ............ C12N 15/1093 506/9 |
| 2015/0299784 A1 | 10/2015 | Fan et al. |
| 2016/0203259 A1 | 7/2016 | Scolnick et al. |

FOREIGN PATENT DOCUMENTS

| | | |
|---|---|---|
| WO | 2012/054873 A3 | 8/2012 |
| WO | 2013/130512 A3 | 10/2013 |
| WO | 2013/138510 A9 | 7/2014 |
| WO | 2014/144092 A1 | 9/2014 |
| WO | 2015/031691 A1 | 3/2015 |

OTHER PUBLICATIONS

Grothues, 1993, PCR amplification of megabase DNA with tagged random primers (T-PCR), Nucl Acids Res 21:1321-1322.

Illumina, 2011, TruSeq RNA and DNA Sample Preparation Kits v2, 1-15 Illumina, dated 27 Apr. 27, 2011 (4 pages).

International Search Report and Written Opinion dated Mar. 5, 2015, in international patent application PCT/US2014/065530, filed Nov. 13, 2014 (12 pages).

Langmead, 2009, Ultrafast and memory-efficient alignment of short DNA sequences to the human genome, Genome Biol 10:R25.

Liu, 2008, Sequence space coverage, entropy of genomes and the potential to detect non-human DNA in human samples, BMC Genomics 9(509):1-17.

Margulies, 2005, Genome sequencing in open microfabricated high density picoliter reactors, Nature 437 (7057):376-380.

McCloskey, 2007, Encoding PCR products with batch-stamps and barcodes, Biochem Genet 45:761-767.

Myers, 2013, Protocol for Creating Multiplexed miRNA Libraries for Use in Illumina Sequencing, Myers lab microRNA-seq Protocol, Hudson Alpha Institute for Biotechnology web site, dated May 2, 2013, (15 pages).

Schiemer, 2011, Illumina TruSeq Adapters Demystified,Tufts University Core Facility XP055357867 (5 pages).

Soni, 2007, Progress toward ultrafast DNA sequencing using solid-state nanopores, Clin Chem 53(11):1996-2001.

Stratagene, 1998, Gene characterization kits, Stratagene Catalog, p. 39 (2 pages).

Trapnell, 2010, Transcript assembly and quantification by RNA-Seq reveals unannotated transcripts and isoform switching during cell differentiation, Nat Biotech 28:511-515.

Trapnell, 2013, Differential analysis of gene regulation at transcript resolution with RNA-seq, Nat Biotech 31:46-53.

Walker, 1992, Strand displacement amplification—an isothermal, in vitro DNA amplification technique, Nucl Acids Res 20(7):1691-1696.

Westin 2000, Anchored multiplex amplification on a microelectronic chip array, Nat Biotech 18:199-204.

\* cited by examiner

MOLECULAR TAG ATTACHMENT AND TRANSFER

BACKGROUND

Next generation sequencing (NGS) techniques provide the means for rapid and cost-effective analysis with an unprecedented level of detail and depth. However, a current problem with the application of NGS platforms is that true low frequency variants often cannot be effectively distinguished from detected variants caused by errors during sample preparation or sequencing. For example, the bases in DNA fragments can undergo chemical modifications during isolation, fixation, storage or processing. These modifications can alter the way that DNA modifying enzymes interact with the DNA fragments. An example of such a modification is the oxidation of a cytosine residue. Once oxidized, a DNA polymerase will no longer recognize this base as a "C" nucleotide; it now recognizes this as a U. In the process of determining the base sequence of this DNA fragment, it is typical for a DNA polymerase to make a copy of the fragment in the library generation process. When the sequence of this fragment is determined, there will be an A/T base pair in place of the original G/C base pair. It will appear as though this fragment had a Single Nucleotide Variant (SNV) in this location. Since the original fragment did not have this variant, it will be a false positive modification. Other fragments representing the same genomic location will not have this variant. However, it would not be possible to tell if this was a processing error or a very low frequency event.

Unambiguous low frequency event determination is particularly important in analyzing materials obtained from liquid biopsy samples. Liquid biopsies are analysis of materials extracted from biological fluids (e.g., blood or plasma). It is hoped that indication of disease can be detected in these samples so more invasive sampling can be avoided. DNA from dead or lysed cells are the typical analytes. Since disease cells make up a very small proportion of total cells within the body, DNA from these cells makes up a very small amount of the DNA present in these biological fluids. Since the consequence of a false positive modification can result in the necessity to obtain an invasive sample for verification, methods for reducing false positive results for low frequency events are needed.

SUMMARY

Described herein are methods, compositions and kits for identifying potential false positive detections in nucleic acid sequencing. Embodiments of the present disclosure relate to a method of determining a modification of a DNA sample. In some embodiments, the method includes preparing a double-stranded DNA fragment linked with a plurality of oligonucleotide adaptors. In some instances, the double-stranded DNA fragment may include a nucleic acid sequence of interest. The double-stranded DNA fragment may be denatured to generate a first strand DNA fragment and a second strand DNA fragment. A first probe may be annealed to the first strand DNA fragment. The first probe may include a probe oligonucleotide sequence that is complementary to and hybridizes to a first probe target region associated with the nucleic acid sequence of interest. The first probe may be extended with a DNA polymerase using the first strand DNA fragment as a template, thereby generating a probe extension sequence.

In some embodiments, a primer or a second probe may be annealed to the second strand DNA fragment. The primer and the second probe may include a tag sequence. An extension sequence may be generated using the primer or the second probe, and the extension sequence may include the tag sequence or a complement of the tag sequence. The extension sequence and the probe extension sequence may be sequenced and the modification of the DNA sample may be determined based on existence or absence of the tag sequence or the complement of the tag sequence.

In some embodiments, the modification comprises a modification of the DNA sample resulting in a false positive single nucleotide polymorphism (SNP) detection.

In some embodiments, the DNA sample comprises a DNA sample in FFPE or a plasma sample.

In some embodiments, the second probe may be annealed to the second strand DNA fragment. The second probe may include a non-extendable probe sequence and a tag sequence, and the non-extendable probe sequence is complementary to and hybridizes to a second probe target region associated with the nucleic acid sequence of interest. A primer sequence may be annealed to 3' end of the second strand DNA fragment, and the primer sequence may be extended with the DNA polymerase using the second strand DNA fragment as a template, thereby generating a primer extension sequence. Further, the primer extension sequence and the second probe may be ligated, thereby generating the extension sequence including the tag sequence. In certain embodiments, the probe extension sequence and the extension sequence may be amplified using PCR primers. In some instances, the second probe may further include a 3' tail oligonucleotide sequence suitable for amplification and/or sequencing, and the primer sequence may further include a 5' tail oligonucleotide sequence suitable for amplification and/or sequencing. For example, the extension sequence may be amplified using a first primer that is directed against the complement of at least a portion of an oligonucleotide adaptor of the plurality of oligonucleotide adaptors and a second primer that is directed against at least a portion of the 5' tail oligonucleotide sequence. The probe extension sequence may be amplified using a third primer that is directed against the complement of at least a portion of the 3' tail oligonucleotide sequence.

In some embodiments, the probe extension sequence and the extension sequence may be sequenced thereby generating a sequencing result. Further, sequencing information of the nucleic acid sequence of interest associated with the first strand DNA fragment and sequencing information of the nucleic acid sequence of interest associated with the second strand DNA fragment may be compared to distinguish true positive and false positive modifications in the nucleic acid of interest may be determined.

In some embodiments, a primer sequence may be annealed to the second strand DNA fragment, the primer sequence including the tag sequence. The primer sequence may be extended with a DNA polymerase using the second strand DNA fragment as a template thereby generating a primer extension sequence. The primer extension sequence and the second strand DNA fragment may be denatured. The second probe may be annealed to the primer extension sequence, and the second probe may include a second probe oligonucleotide sequence that is complementary to and hybridizes to a second probe target region associated with the nucleic acid sequence of interest. The second probe annealed to the primer extension sequence may be extended with the DNA polymerase using the primer extension sequence as a template, thereby generating the extension sequence including a sequence complementary to the tag sequence. In some instances, the primer sequence may further include at least a portion of the oligonucleotide adaptor and a 5' tail oligonucleotide sequence, and the second probe may further include a 5' tail oligonucleotide sequence.

In some embodiments, the DNA sample may be fragmented, thereby generating the double-stranded DNA fragment including the nucleic acid sequence of interest. An oligonucleotide adaptor may be ligated to each 5' end of the double-stranded DNA fragment, and the oligonucleotide adaptor may include a priming site, a barcode, and/or a variable sequence or a random sequence. The 3' ends of the double-stranded DNA fragment may be extended with a DNA polymerase using two strands of the double-stranded DNA fragment as a template, respectively. In some instances, the barcode may include an oligonucleotide sequence capable of identifying the DNA sample, and the variable sequence may include an oligonucleotide sequence capable of marking duplicate sequencing reads. In some embodiments, a first oligonucleotide adaptor may be ligated to the 5' end of a first strand of the double-stranded DNA fragment, and the first oligonucleotide adaptor may include an index priming site, a first barcode, and a first variable sequence. A second oligonucleotide adaptor may be ligated to the 5' end of a second strand of the double-stranded DNA fragment, and the second oligonucleotide adaptor may include the index priming site, a second barcode, and a second variable sequence. In some instances, the first barcode and the second barcode are identical. The first oligonucleotide adaptor may further include a forward sequencing primer sequence, and the second oligonucleotide adaptor may further include the forward sequencing primer sequence.

Some embodiments of the present disclosure further relate to a method of identifying modifications in nucleic acid sequencing of DNA templates that could lead to false positive SNV calls. In some embodiments, the method may include preparing a double-stranded DNA fragment linked with a plurality of oligonucleotide adaptors. For example, the double-stranded DNA fragment may include a nucleic acid sequence of interest. In some embodiments, the double-stranded DNA fragment may be denatured, thereby generating a first strand DNA fragment and a second strand DNA fragment. A first probe may be annealed to the first strand DNA fragment, and the first probe may include a probe oligonucleotide sequence that is complementary to and hybridizes to a first probe target region associated with the nucleic acid sequence of interest. The first probe may then be extended with a DNA polymerase using the first strand DNA fragment as a template, thereby generating a probe extension sequence. A second probe may be annealed to the second strand DNA fragment, and the second probe may include a non-extendable probe sequence and a tag sequence. In some instances, the non-extendable probe sequence is complementary to and hybridizes to a second probe target region associated with the nucleic acid sequence of interest. In some embodiments, a primer sequence may be annealed to the 3' end of the second strand DNA fragment, and the primer sequence may be extended with the DNA polymerase using the second strand DNA fragment as a template, thereby generating a primer extension sequence. In some instances, the primer extension sequence and the second probe may be ligated, thereby generating the ligated primer extension sequence including the tag sequence. The ligated primer extension sequence and the probe extension sequence may be sequenced, and the sequences can be compared to verify a positive modification or a false positive.

In some embodiments, the approach may detect a false positive single nucleotide polymorphism (SNP) or a true positive SNP in the DNA sequence of interest In some embodiments, the DNA sample may be derived from a FFPE material or plasma.

In some embodiments, the probe extension sequence and the ligated primer extension sequence may be amplified using PCR primers.

In some embodiments, the second probe may further include a 3' tail oligonucleotide sequence suitable for amplification and/or sequencing, and the primer sequence may further include a 5' tail oligonucleotide sequence suitable for amplification and/or sequencing. In some instances, the ligated primer extension sequence may be amplified using a first primer that is directed against the complement of at least a portion of an oligonucleotide adaptor of the plurality of oligonucleotide adaptors and a second primer that is directed against at least a portion of the 5' tail oligonucleotide sequence. The probe extension sequence may be amplified using a third primer that is directed against the complement of at least a portion of the 3' tail oligonucleotide sequence. In some embodiments, the probe extension sequence and the ligated primer extension sequence may be sequenced, thereby generating a sequencing result. Further, sequencing information of the nucleic acid sequence of interest associated with the first strand DNA fragment and sequencing information of the nucleic acid sequence of interest associated with the second strand DNA fragment may be compared to distinguish true positive and false positive modifications in the nucleic acid of interest may be determined.

In some embodiments, the double-stranded DNA fragment including the nucleic acid sequence of interest may be generated. An oligonucleotide adaptor may be ligated to each 5' end of the double-stranded DNA fragment, and the oligonucleotide adaptor may include a priming site, a barcode, and a variable sequence. The 3' ends of the double-stranded DNA fragment may be extended with a DNA polymerase using two strands of the double-stranded DNA fragment as a template, respectively. In some instances, the barcode may include an oligonucleotide sequence capable of identifying the DNA sample, and the variable sequence may include an oligonucleotide sequence capable of marking duplicate sequencing reads. In some embodiments, a first oligonucleotide adaptor may be ligated to the 5' end of a first strand of the double-stranded DNA fragment, and the first oligonucleotide adaptor may include an index priming site, a first barcode, and a first variable sequence. A second oligonucleotide adaptor may be ligated to the 5' end of a second strand of the double-stranded DNA fragment, and the second oligonucleotide adaptor may include the index priming site, a second barcode, and a second variable sequence. In some instances, the first barcode and the second barcode are identical. In some instances, the first oligonucleotide adaptor may further include a forward sequencing primer sequence, and the second oligonucleotide adaptor may further include the forward sequencing primer sequence.

Some embodiments of present disclosure further relate to another method of identifying a false positive modification in nucleic acid sequencing of a DNA sample. The method may include preparing a double-stranded DNA fragment linked with a plurality of oligonucleotide adaptors. The double-stranded DNA fragment may include a nucleic acid sequence of interest. The double-stranded DNA fragment may be denatured to generate a first strand DNA fragment and a second strand DNA fragment. A first probe may be annealed to the first strand DNA fragment, and the first probe may include a probe oligonucleotide sequence that is complementary to and hybridizes to a first probe target region associated with the nucleic acid sequence of interest. The first probe may be extended with a DNA polymerase using the first strand DNA fragment as a template, thereby generating a probe extension sequence. A primer sequence may be annealed to the second strand DNA fragment, the primer sequence including a tag sequence. The primer sequence may be further extended with a DNA polymerase using the second strand DNA fragment as a template thereby generating a primer extension sequence. Then, the primer extension sequence and the second strand DNA fragment may be denatured, and a second probe may be annealed to the primer extension sequence. For example, the second probe may include a second probe oligonucleotide sequence that is complementary to and hybridizes to a second probe target region associated with the nucleic acid sequence of interest. The second probe annealed to the primer extension sequence may be further extended with the DNA polymerase using the primer extension sequence as a template, thereby generating an additional probe extension sequence including a sequence complementary to the tag sequence. Accordingly, the probe extension sequence and the additional probe extension sequence may be sequenced, and compared to distinguish true and false positive modifications in nucleic acid sequencing.

In some embodiments, the primer sequence may further include at least a portion of the oligonucleotide adaptor and a 5' tail oligonucleotide sequence.

In some embodiments, the second probe may further include a 5' tail oligonucleotide sequence.

In some embodiments, the DNA sample may be fragmented, thereby generating the double-stranded DNA fragment including the nucleic acid sequence of interest. An oligonucleotide adaptor may be ligated to each 5' end of the double-stranded DNA fragment, and the oligonucleotide adaptor may include a priming site, a barcode, and a variable sequence or a random sequence. The 3' ends of the double-stranded DNA fragment may be extended with a DNA polymerase using two strands of the double-stranded DNA fragment as a template, respectively. In some embodiments, the barcode may include an oligonucleotide sequence capable of identifying the DNA sample. In some embodiments, the variable sequence may include an oligonucleotide sequence capable of marking duplicate sequencing reads. In some instances, a first oligonucleotide adaptor may be ligated to the 5' end of a first strand of the double-stranded DNA fragment, and the first oligonucleotide adaptor may include an index priming site, a first barcode, and a first variable sequence. A second oligonucleotide adaptor may be ligated to the 5' end of a second strand of the double-stranded DNA fragment, and the second oligonucleotide adaptor may include the index priming site, a second barcode, and a second variable sequence. For example, the first barcode and the second barcode are identical. In some embodiments, the first oligonucleotide adaptor may further include a forward sequencing primer sequence, and the second oligonucleotide adaptor may further include the forward sequencing primer sequence.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

DETAILED DESCRIPTION

Figure 1:
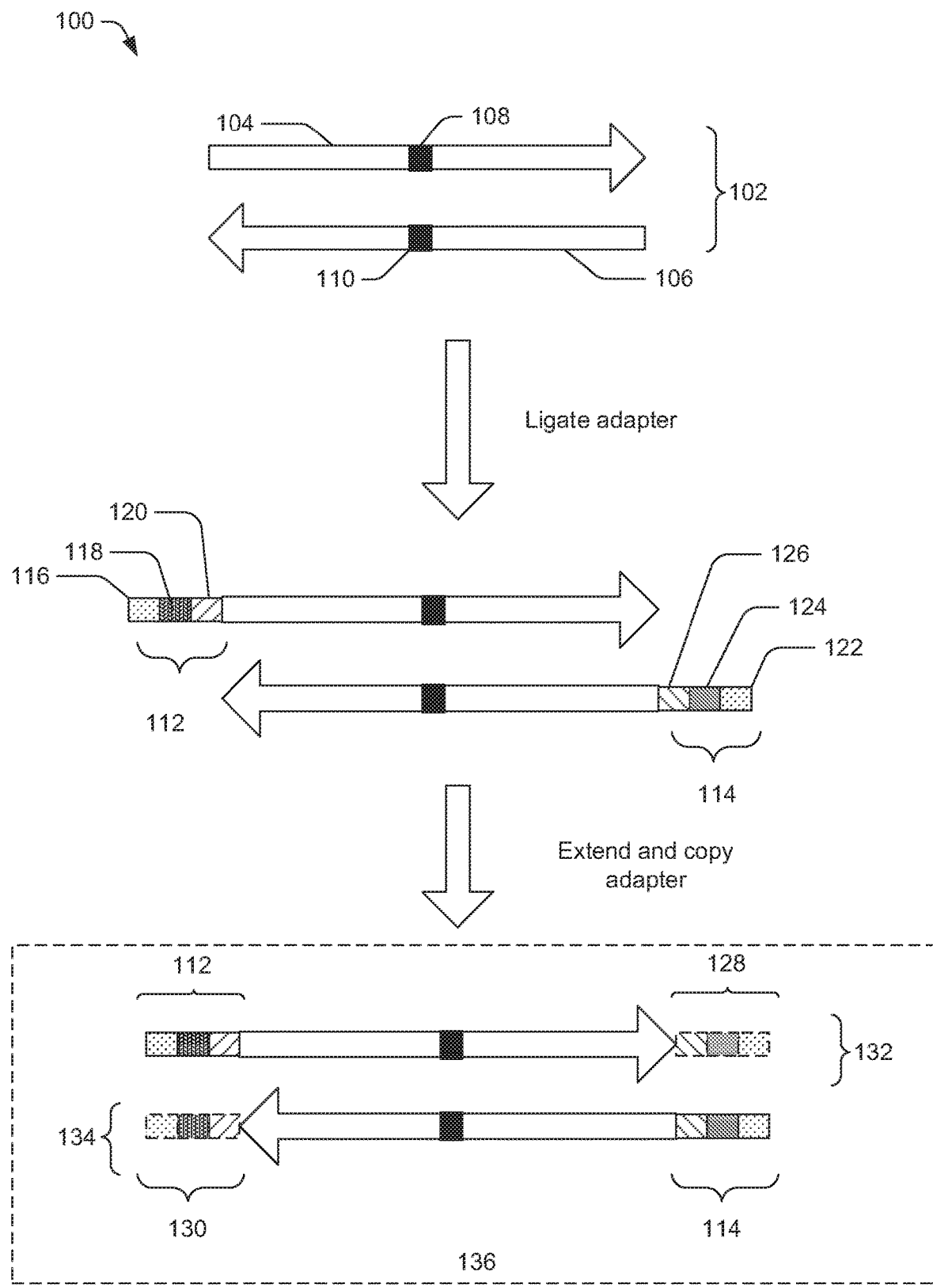
FIG. 1 is a diagram illustrating an exemplary process to generate a nucleic acid fragment linked with one or more adaptors.

Described herein are methods, compositions and kits for distinguishing false positive modifications from true positive modifications (e.g., SNV) in nucleic acid sequencing. Embodiments of the present disclosure include ligating oligonucleotide adaptors onto the 5' ends of an individual DNA fragment derived from a DNA sample. Multiple probes and/or primers are used to link a tag sequence to one strand DNA fragment of the individual DNA fragment to be distinguishable from another strand DNA fragment. Because the oligonucleotide adaptors include a barcode and/or other identifiable sequences, sequence data from these two strand DNA fragments can be compared with each other after DNA fragments are separated in the sequencing processes. Because of the linked tag sequence, true positive SNVs can be distinguished from false positive SNVs. Low frequency events can be recognized since true positives will have sequence supporting a base change in data obtained from both strand DNA fragments, while a false positive will suggest a change in only one strand DNA fragment.

Conventional techniques such as deep sequencing and consensus sequence determination can reduce sequencer errors. These techniques describe appending a tag or variable sequence to DNA fragments early in a library generation process. Once sequenced, all fragments possessing this tag should have identical sequence. The consensus or most common sequence reflects the original DNA fragment sequence; any low frequency event is the result of a processing error. Unfortunately, while improving sequence accuracy, it cannot recognize errors present in the original template that are introduced in the initial copying step. The present disclosure describes a scalable means of identifying low frequency events of variants that does not require attachment of complementary tags on each end of every DNA fragment.

Unless otherwise specified, terms and symbols of biochemistry, nucleic acid chemistry, molecular biology and molecular genetics follow those of standard treatises and texts in the field.

As used herein and in the appended claims, the singular forms "a," "an," and "the" include plural referents unless the context clearly dictates otherwise. Thus, for example, reference to "a polymerase" can refer to one agent or to mixtures of such agents, and reference to "the method" includes reference to equivalent steps and/or methods known to those skilled in the art, and so forth.

The term "adaptor", as used herein, can refer to an oligonucleotide of known sequence, the attachment of which to a specific nucleic acid sequence or a target polynucleotide strand of interest enables the generation of amplification-ready products of the specific nucleic acid or the target polynucleotide strand of interest. The specific nucleic acid samples can be fragmented or not prior to the addition of at least one adaptor.

Various adaptor designs are envisioned which are suitable for generation of amplification-ready products of specific sequence regions/strands of interest. For example, when double stranded adaptors are used, the two strands of the adaptor can be self-complementary, non-complementary or partially complementary. Adaptors can contain at least a partial forward sequence priming site and a random sequence.

In some embodiments, adaptors comprise an additional identifier sequence, e.g., a barcode sequence. As used herein, the term "barcode" can refer to a known nucleic acid sequence that allows some feature of a polynucleotide with which the barcode is associated to be identified. In some embodiments, the feature of the polynucleotide to be identified can be the sample from which the polynucleotide is derived. A barcode can, for example, comprise a nucleic acid sequence that when joined to a target polynucleotide can serve as an identifier of the sample from which the target polynucleotide was derived. In some embodiments, barcodes are at least three or more nucleotides in length. In some embodiments, barcodes are shorter than ten nucleotides in length. In some embodiments, each barcode in a plurality of barcodes differ from every other barcode in the plurality at least three nucleotide positions. In some embodiments, barcodes associated with some polynucleotides are of different length than barcodes associated with other polynucleotides. Barcodes can be of sufficient length and comprise sequences that are sufficiently different to allow the identification of samples based on barcodes with which they are associated. In some embodiments, both the forward and reverse adaptor can comprise at least one of a plurality of barcode sequences. In some embodiments, the first and second adaptor may include at least one of a plurality of barcode sequences. In some embodiments, each reverse adaptor may include at least one of a plurality of barcode sequences, wherein each barcode sequence of the plurality of barcode sequences differs from every other barcode sequence in the plurality of barcode sequences. In some embodiments, both the first adaptor and the second adaptor comprise at least one of a plurality of barcode sequences. In some embodiments, barcodes for second adaptor oligonucleotides are selected independently from barcodes for first adaptor oligonucleotides. In some embodiments, first adaptor oligonucleotides and second adaptor oligonucleotides having barcodes are paired, such that adaptors of the pair comprise the same or different one or more barcodes. In some embodiments, the methods of the disclosure further comprise identifying the sample from which a target polynucleotide can be derived based on the barcode sequence to which the target polynucleotide is joined.

Appending of an adaptor(s) at the desired end of the sequence region(s) of interest utilizing ligation can be suitable for carrying out the disclosed methods. Various ligation modalities are envisioned, dependent on the choice of nucleic acid, nucleic acid modifying enzymes and the resulting ligatable end of the nucleic acid. For example, when a blunt end product including the target region/sequence of interest can be generated, blunt end ligation can be suitable. Alternatively, where the cleavage can be carried out using a restriction enzyme of known sequence specificity, leading to the generation of cleavage sites with known sequence overhangs, suitable ends of the adaptors can be designed to enable hybridization of the adaptor to the cleavage site of the sequence region of interest and subsequent ligation. Ligation also can refer to any joining of two nucleic acid molecules that results in a single nucleic acid sequences that can be further modified to obtain the sequence of the nucleic acids in question.

As used herein, the terms "amplifying", "amplification" and to "amplify" a specific nucleic acid as used herein, can refer to a procedure wherein multiple copies of the nucleic acid sample of interest are generated, for example, in the form of DNA copies. Many methods and protocols are known in the art to amplify nucleic acids, such as e.g., PCR and qPCR.

As used herein, the term "cDNA" as used herein, can refer to complementary DNA. The DNA can be synthesized in a reaction catalyzed by reverse transcriptase and DNA polymerase from a messenger RNA (mRNA) template.

As used herein, the term "complementary" as used herein, can refer to complementarity to all or only to a portion of a sequence. The number of nucleotides in a hybridizable sequence of a specific oligonucleotide primer or probe can be such that stringency conditions used to hybridize the oligonucleotide primer or probe can prevent excessive random non-specific hybridization. The number of nucleotides in the hybridizing portion of the oligonucleotide primer or probe can be at least as great as the defined sequence on the target polynucleotide that the oligonucleotide primer or probe hybridizes to usually about 20 to about 50 nucleotides. The target polynucleotide/oligonucleotide can be larger than the oligonucleotide primer, primers or probe.

As used herein, the term "denaturing" as used herein, can refer to the separation of double stranded nucleic acid into single strands. Denaturation can be achieved using any of the methods known in the art including, but not limited to, physical, thermal, and/or chemical denaturation.

As used herein, the acronym "FFPE" as used herein denotes Formalin-Fixed, Paraffin Embedded. FFPE is a method used in preservation of a tissue sample in which the sample can be fixed in a formalin solution coupled with application of a wax referred to as paraffin.

As used herein, the phrase "genomic DNA" as used herein, can refer to chromosomal DNA, abbreviated as gDNA for genomic deoxyribonucleic acid. gDNA includes the genetic material of an organism.

As used herein, the term "genome" as used herein, can refer to sequences, either DNA, RNA or cDNA derived from a patient, a tissue, an organ, a single cell, a tumor, a specimen of an organic fluid taken from a patient, freely circulating nucleic acid, a fungus, a prokaryotic organism and a virus.

As used herein, the term "transcriptome" can be all RNA sequences that can reflect a partial or entire expressed genome of an organism.

As used herein, the term "kit" can refer to any system for delivering materials. In the context of reaction assays, such delivery systems can include elements allowing the storage, transport, or delivery of reaction components such as oligonucleotides, buffering components, additives, reaction enhancers, enzymes and the like in the appropriate containers from one location to another commonly provided with written instructions for performing the assay. Kits can include one or more enclosures or boxes containing the relevant reaction reagents and supporting materials. The kit can comprise two or more separate containers wherein each of those containers includes a portion of the total kit components. The containers can be delivered to the intended recipient together or separately.

As used herein, the phrase "nucleic acid (NA)-modifying enzyme" as used herein, can refer to a DNA-specific modifying enzyme. The NA-modifying enzyme can be selected for specificity for double-stranded DNA. The enzyme can be a duplex-specific endonuclease, a blunt-end frequent cutter restriction enzyme, or other restriction enzyme.

As used herein, the phrases "nucleic acid fragment" and "specific nucleic acid" are used interchangeably and as used herein, can refer to a portion of a nucleic acid sample. The nucleic acids in the input sample can be fragmented into a population of fragmented nucleic acid molecules or to polynucleotides of one or more specific size range(s).

As used herein, the phrase "specific nucleic acid sequence" or "specific sequence" as used herein, can be a polynucleotide sequence of interest, for which digital measurement and/or quantitation is desired, including but not limited to a nucleic acid fragment. The specific sequence can be known or not known, in terms of its actual sequence. A "template", as used herein, can be a polynucleotide that contains the specific nucleic acid sequence. The terms "specific sequence," "specific nucleic acid sequence," "specific nucleotide sequence," "regions of interest," or "sequence of interest" and, variations thereof, are used interchangeably.

As used herein, the phrases "qualified nucleic acid" and "qualifies the target nucleic acid fragment" as used herein, can refer to a fragment of a gDNA or RNA sequence that is: i.) an acceptable template for a DNA polymerase, i.e. the template can be free of cross-links or inhibitors to the DNA polymerase, or ii.) the template has a modification including, but not limited to, attachment at the 5' and/or 3' end a polynucleotide sequence at least one of a barcode, an adaptor, a sequence complementary to a primer and so on such that the fragment can be modified for purposes of quantitation, amplification, detection or to other methods known to one of skill in the art of gDNA and cDNA sequence analyses. The presence of inhibitors can be the result of using gDNA obtained from a tissue sample that had undergone fixation in a FFPE preparation.

As used herein, the term "oligonucleotide" can refer to a polynucleotide chain, typically less than 200 residues long, e.g., between 15 and 100 nucleotides long, but can also encompass longer polynucleotide chains. Oligonucleotides can be single- or double-stranded. As used in this disclosure, the term "oligonucleotide" can be used interchangeably with the terms "primer", "probe" and "adaptor".

As used herein, "PCR" is an abbreviation of term "polymerase chain reaction," a commonly available nucleic acids amplification technology. In some embodiments, PCR employs two oligonucleotide primers for each strand that are designed such as extension of one primer provides a template for another primer in the next PCR cycle. Either one of a pair of oligonucleotide primers can be named herein as a "forward" or "reverse" primer with the purpose of distinguishing the oligonucleotide primers in discussion. A PCR can consist of repetition (or cycles) of (i) a denaturation step which separates the strands of a double stranded nucleic acid, followed by (ii) an annealing step, which allows primers to anneal to positions flanking a sequence of interest; and then (iii) an extension step which extends the primers in a 5' to 3' direction thereby forming a nucleic acid fragment complementary to the target sequence. Each of the above steps can be conducted at a different temperature using an automated thermocycler. The PCR cycles can be repeated as often as desired resulting in an exponential accumulation of a target DNA fragment whose termini are usually defined by the 5' ends of the primers used.

The phrase "quantitative PCR" or "qPCR", as used herein, can refer to a PCR designed to measure the abundance of one or more specific target sequences in a sample. Quantitative measurements can be made using one or more reference nucleic acid sequences that can be assayed separately or together with a target nucleic acid.

The term "portion", as used herein, can refer to less than the total length of a nucleic acid sequence, a nucleic acid sequence fragment, a specific nucleic acid sequence, a specific nucleic acid fragment, a probe, a primer and the like.

The term "primer", as used herein, can refer to an oligonucleotide, generally with a free 3' hydroxyl group, that can be capable of hybridizing or annealing with a template (such as a specific polynucleotide, target DNA, target RNA, a primer extension product or a probe extension product) and can be also capable of promoting polymerization of a polynucleotide complementary to the template. A primer can contain a non-hybridizing sequence that constitutes a tail of the primer. A primer can hybridize to a target even though its sequences are not fully complementary to the target.

The primers utilized herein can be oligonucleotides that are employed in an extension reaction by a polymerase along a polynucleotide template, such as in PCR, qPCR, an extension reaction and the like. The oligonucleotide primer can be a synthetic polynucleotide that can be single stranded, containing a sequence at its 3'-end that can be capable of hybridizing with a sequence of the target polynucleotide.

The 3' region of the primer that hybridizes with the specific nucleic acid can comprise at least 80%, preferably 90%, more preferably 95%, most preferably 100%, complementarity to a sequence or to a primer binding site.

The term, "tail sequence" can refer to a non-hybridizing sequence adjacent to and 5' of a primer or probe sequence. The term "probe extension product" can refer to a DNA fragment resulting from the hybridization of a probe and template directed synthesis initiated from the probe, e.g., within a specific nucleic acid sequence. The probe can be extended by a polymerase into an adaptor sequence, if present and appended to the specific nucleic acid. The resulting probe extension product can have both a first adaptor, e.g., the adaptor appended to the specific nucleic acid sequence and a second adaptor, e.g., found within the tail sequence of the primer or probe.

As used herein, a "random" primer, oligonucleotide, nucleotide or nucleotide sequence may include a sequence that can be designed not necessarily based on a particular or to a specific sequence in a sample, but rather can be based on a statistical expectation (or an empirical observation) that the sequence of the random primer can be hybridizable or related (under a given set of conditions) to one or more sequences in the sample.

As used herein, the notation "n-random" primer, oligonucleotide, nucleotide or nucleotide sequence can refer to a defined number (n) of bases.

As used herein, a "variable sequence" or a "variable nucleotide sequence" refers to a certain type of random nucleotides of which one or more nucleotides are selected from a subset of nucleotides such that certain positions specifically exclude certain bases. For example, 8 random nucleotides ("N8") is represented by "NNNNNNNN," and an 8 variable sequence may be represented by "NHNNHNHN", wherein the N represents a randomly selected nucleotide from all 4 nucleotides (A, T, C or G) and H represents a randomly selected nucleotide from only a subset of 3 nucleotides (e.g., A, T, or C, but not G).

The term, "sample" as used herein, can refer to any substance containing or presumed to contain a nucleic acid of interest, and thus includes a sample of nucleic acid, cells, organisms, tissue, fluids (e.g., spinal fluid or lymph fluids), organic fluid taken from a patient, and sample including but not limited to blood, plasma, serum, urine, tears, stool, respiratory and genitourinary tracts, saliva, fragments of different organs, tissue, blood cells, circulating tumor cell (CTC) or a disseminated tumor cell (CTD), bone, samples of in vitro cell cultures or specimens that have been suspected to contain nucleic acid molecules.

The term "PCR duplicate", as used herein, can refer to any sequencing read that is derived from the same original nucleic acid molecule and so, the same primer/probe extension product sequence, as another sequencing read and is therefore not representative of a unique nucleic acid molecule.

The term "probe", as used herein, can refer to an oligonucleotide sequence. The probe can be complementary to a probe target region. The probe sequence complementary to the probe target region can be less than about 200 residues long, between about 15 and 100 nucleotides long, but can also be intended to encompass longer polynucleotide chains. Probe target regions can be single- or double-stranded. The probe target region provides a hybridization site for a complementary probe that undergoes extension using a polymerase.

The term "probe target region", as used herein, can refer to a region within a genomic or transcriptomic database or within a genome or transcriptome sequence to which a probe has been designed. The region may extend beyond the specific complementary region and include flanking regions of the genome or transcriptome. The aligned probe sequence to its probe target region can provide verification of the specificity of probe annealing and so too the probe extension product and thus the specific nucleic acid molecule being counted.

The probe target region is within a specific nucleic acid sequence. The probe target region can be about 500 residues long and can also be between about 80 and 1000 residues. As used herein, the term "probe target region" can be used interchangeably with the term "probe hybridization site" and "probe annealing site".

The term "non-extendable probe" refers to an oligonucleotide that is made non-extendable by, for example, adding bases to the 3' end that are not complementary to the target sequence and therefore do not base-pair and cannot be enzymatically extended.

The terms "tag sequence" refers to a sequence established in order to easily screen for a molecule having the tag sequence from a molecule without the tag sequence in various assays. The tag sequence is not particularly limited, as long as it has a strand length and sequence appropriate for the purpose of the present disclosure, and any sequence can be used.

Additional information related to definitions, processes, methods structures, and other embodiments is provided in U.S. Pat. Pub. No. US20160203259, assigned to Nugen Corp., and incorporated by reference in its entirety.

Embodiments relate to a method of determining a modification of a DNA sample. In some embodiments, the method includes preparing a double-stranded DNA fragment linked with a plurality of oligonucleotide adaptors. In some instances, the double-stranded DNA fragment may include a nucleic acid sequence of interest. The double-stranded DNA fragment may be denatured to generate a first strand DNA fragment and a second strand DNA fragment. A first probe may be annealed to the first strand DNA fragment. The first probe may include a probe oligonucleotide sequence that is complementary to and hybridizing to a first probe target region associated with the nucleic acid sequence of interest. The first probe may be extended with a DNA polymerase using the first strand DNA fragment as a template, thereby generating a probe extension sequence. A primer or a second probe may be annealed to the second strand DNA fragment. The primer and the second probe may include a tag sequence. An extension sequence may be generated using the primer or the second probe, and the extension sequence may include the tag sequence or a complement of the tag sequence. The extension sequence and the probe extension sequence may be sequenced and the modification of the DNA sample may be determined based on existence or absence of the tag sequence or a complement of the tag sequence.

In some embodiments, the modification may include a modification of the DNA sample resulting in a false positive single nucleotide polymorphism (SNP) detection.

In some embodiments, the DNA sample may be derived from a FFPE material or plasma.

In some embodiments, the second probe may be ligated to the second strand DNA fragment. The second probe may include a non-extendable probe sequence and a tag sequence, and the non-extendable probe sequence is complementary to and hybridizes to a second probe target region associated with the nucleic acid sequence of interest. A primer sequence may be annealed to 3' end of the second strand DNA fragment, and the primer sequence may be extended with the DNA polymerase using the second strand DNA fragment as a template, thereby generating a primer extension sequence. Then, the primer extension sequence and the second probe may be ligated thereby generating the extension sequence including the tag sequence. In certain embodiments, the probe extension sequence and the extension sequence may be amplified using PCR primers. In some instances, the second probe may further include a 3' tail oligonucleotide sequence suitable for amplification and/or sequencing, and the primer sequence may further include a 5' tail oligonucleotide sequence suitable for amplification and/or sequencing. For example, the extension sequence may be amplified using a first primer that is directed against the complement of at least a portion of an oligonucleotide adaptor of the plurality of oligonucleotide adaptors and a second primer that is directed against at least a portion of the 5' tail oligonucleotide sequence. The probe extension sequence may be amplified using a third primer that is directed against the complement of at least a portion of the 3' tail oligonucleotide sequence.

In some embodiments, the probe extension sequence and the extension sequence may be sequenced thereby generating a sequencing result. Further, sequencing information of the nucleic acid sequence of interest associated with the first strand DNA fragment and sequencing information of the nucleic acid sequence of interest associated with the second strand DNA fragment may be compared to distinguish true positive and false positive modifications in the nucleic acid of interest may be determined.

In some embodiments, a primer sequence may be annealed to the second strand DNA fragment, the primer sequence including the tag sequence. The primer sequence may be extended with a DNA polymerase using the second strand DNA fragment as a template thereby generating a primer extension sequence. The primer extension sequence and the second strand DNA fragment may be denatured. The second probe may be annealed to the primer extension sequence, and the second probe may include a second probe oligonucleotide sequence that is complementary to and hybridizes to a second probe target region associated with the nucleic acid sequence of interest. The second probe annealed to the primer extension sequence may be extended with the DNA polymerase using the primer extension sequence as a template, thereby generating the extension sequence including a sequence complementary to the tag sequence. In some instances, the primer sequence may further include at least a portion of the oligonucleotide adaptor and a 5' tail oligonucleotide sequence, and the second probe may further include a 5' tail oligonucleotide sequence.

In some embodiments, the DNA sample may be fragmented, thereby generating the double-stranded DNA fragment including the nucleic acid sequence of interest. An oligonucleotide adaptor may be ligated to each 5' end of the double-stranded DNA fragment, and the oligonucleotide adaptor may include a priming site, a barcode, and a variable sequence or a random sequence. The 3' ends of the double-stranded DNA fragment may be extended with a DNA polymerase using two strands of the double-stranded DNA fragment as a template, respectively. In some instances, the barcode may include an oligonucleotide sequence capable of identifying the DNA sample, and the variable sequence may include an oligonucleotide sequence capable of marking duplicate sequencing reads. In some embodiments, a first oligonucleotide adaptor may be ligated to the 5' end of a first strand of the double-stranded DNA fragment, and the first oligonucleotide adaptor may include an index priming site, a first barcode, and a first variable sequence. A second oligonucleotide adaptor may be ligated to the 5' end of a second strand of the double-stranded DNA fragment, and the second oligonucleotide adaptor may include the index priming site, a second barcode, and a second variable sequence. In some instances, the first barcode and the second barcode are identical. The first oligonucleotide adaptor may further include a forward sequencing primer sequence, and the second oligonucleotide adaptor may further include the forward sequencing primer sequence.

The embodiments of the present disclosure further relate to a method of distinguishing a false positive modification from a true positive modification in nucleic acid sequencing of a DNA sample. In some embodiments, the method may include preparing a double-stranded DNA fragment linked with a plurality of oligonucleotide adaptors. For example, the double-stranded DNA fragment may include a nucleic acid sequence of interest. The double-stranded DNA fragment may be denatured, thereby generating a first strand DNA fragment and a second strand DNA fragment. A first probe may be annealed to the first strand DNA fragment, and the first probe may include a probe oligonucleotide sequence that is complementary to and hybridizes to a first probe target region associated with the nucleic acid sequence of interest. The first probe may then be extended with a DNA polymerase using the first strand DNA fragment as a template, thereby generating a probe extension sequence. A second probe may be annealed to the second strand DNA fragment, and the second probe may include a non-extendable probe sequence and a tag sequence. In some instances, the non-extendable probe sequence is complementary to and hybridizes to a second probe target region associated with the nucleic acid sequence of interest. In some embodiments, a primer sequence may be annealed to 3' end of the second strand DNA fragment, and the primer sequence may be extended with the DNA polymerase using the second strand DNA fragment as a template, thereby generating a primer extension sequence. In some instances, the primer extension sequence and the second probe may be ligated thereby generating the ligated primer extension sequence including the tag sequence. The ligated primer extension sequence and the probe extension sequence may be sequenced, and the sequences can be compared to verify a positive modification or a false positive.

In some embodiments, the probe extension sequence and the ligated primer extension sequence may be amplified using PCR primers.

In some embodiments, the second probe may further include a 3' tail oligonucleotide sequence suitable for amplification and/or sequencing, and the primer sequence may further include a 5' tail oligonucleotide sequence suitable for amplification and/or sequencing. In some instances, the ligated primer extension sequence may be amplified using a first primer that is directed against the complement of at least a portion of an oligonucleotide adaptor of the plurality of oligonucleotide adaptors and a second primer that is directed against at least a portion of the 5' tail oligonucleotide sequence. The probe extension sequence may be amplified using a third primer that is directed against the complement of at least a portion of the 3' tail oligonucleotide sequence. In some embodiments, the probe extension sequence and the ligated primer extension sequence may be sequenced thereby generating a sequencing result. Further, sequencing information of the nucleic acid sequence of interest associated with the first strand DNA fragment and sequencing information of the nucleic acid sequence of interest associated with the second strand DNA fragment may be compared to distinguish true positive and false positive modifications in the nucleic acid of interest may be determined.

For example, the methods of the disclosure can be useful for sequencing by the method commercialized by Illumina, Inc., including embodiments as described in U.S. Pat. Nos. 5,750,341; 6,306,597; and 5,969,119. Double stranded fragment polynucleotides can be prepared by the methods of the present disclosure to produce amplified nucleic acid sequences tagged at one (e.g., (A)/(A') or both ends (e.g., (A)/(A') and (C)/(C')). In some cases, single stranded nucleic acid tagged at one or both ends can be amplified by the methods of the present disclosure (e.g., by SPIA or linear PCR). The resulting nucleic acid can then be denatured and the single-stranded amplified polynucleotides can be randomly attached to the inside surface of flow-cell channels. Unlabeled nucleotides can be added to initiate solid-phase bridge amplification to produce dense clusters of double-stranded DNA. To initiate the first base sequencing cycle, four labeled reversible terminators, primers, and DNA polymerase can be added. After laser excitation, fluorescence from each cluster on the flow cell can be imaged. The identity of the first base for each cluster can then be recorded. Cycles of sequencing can be performed to determine the fragment sequence one base at a time.

The present disclosure is not limited to Illumina based sequencing technologies. Other sequencing techniques can also be used. For example, either semiconductor sequencing such as Ion Torrent™ Next-Generation Sequencing Technology provided by Thermo Fisher Scientific, Inc. or nanopore sequencing such as developed by Oxford Nanopore Technologies Ltd, can be used in disclosed embodiments herein.

In some embodiments, the methods of the disclosure can be useful for preparing target polynucleotides for sequencing by the sequencing by ligation methods initially commercialized by Applied Biosystems (e.g., SOLiD sequencing) and now provided by Thermo Fisher Scientific, Inc. In other embodiments, the methods can be useful for preparing target polynucleotides for sequencing by synthesis using methods initially commercialized by 454 Life Sciences and now provided by Roche Life Sciences, Inc.

In some embodiments, the double-stranded DNA fragment including the nucleic acid sequence of interest may be generated. An oligonucleotide adaptor may be ligated to each 5' end of the double-stranded DNA fragment, and the oligonucleotide adaptor may include a priming site, a barcode, and a variable sequence or a random sequence. The 3' ends of the double-stranded DNA fragment may be extended with a DNA polymerase using two strands of the double-stranded DNA fragment as a template, respectively. In some instances, the barcode may include an oligonucleotide sequence capable of identifying the DNA sample, and the variable sequence may include an oligonucleotide sequence capable of marking duplicate sequencing reads. In some embodiments, a first oligonucleotide adaptor may be ligated to the 5' end of a first strand of the double-stranded DNA fragment, and the first oligonucleotide adaptor may include an index priming site, a first barcode, and a first variable sequence. A second oligonucleotide adaptor may be ligated to the 5' end of a second strand of the double-stranded DNA fragment, and the second oligonucleotide adaptor may include the index priming site, a second barcode, and a second variable sequence. In some instances, the first barcode and the second barcode are identical. In some instances, the first oligonucleotide adaptor may further include a forward sequencing primer sequence, and the second oligonucleotide adaptor may further include the forward sequencing primer sequence.

The embodiments of present disclosure further relate to another method of distinguishing a false positive modification from a true positive modification in nucleic acid sequencing of a DNA sample. The method may include preparing a double-stranded DNA fragment linked with a plurality of oligonucleotide adaptors. The double-stranded DNA fragment may include a nucleic acid sequence of interest. The double-stranded DNA fragment may be denatured to generate a first strand DNA fragment and a second strand DNA fragment. A first probe may be annealed to the first strand DNA fragment, and the first probe may include a probe oligonucleotide sequence that is complementary to and hybridizes to a first probe target region associated with the nucleic acid sequence of interest. The first probe may be extended with a DNA polymerase using the first strand DNA fragment as a template, thereby generating a probe extension sequence. A primer sequence may be annealed to the second strand DNA fragment, the primer sequence including a tag sequence. The primer sequence may be further extended with a DNA polymerase using the second strand DNA fragment as a template thereby generating a primer extension sequence. Then, the primer extension sequence and the second strand DNA fragment may be denatured, and a second probe may be annealed to the primer extension sequence. For example, the second probe may include a second probe oligonucleotide sequence that is complementary to and hybridizes to a second probe target region associated with the nucleic acid sequence of interest. The second probe annealed to the primer extension sequence may be further extended with the DNA polymerase using the primer extension sequence as a template, thereby generating an additional probe extension sequence including a sequence complementary to the tag sequence. Accordingly, the sequencing information of probe extension sequence and the additional probe extension sequence may be compared to distinguish true positive and false positive modifications in the nucleic acid of interest may be determined.

In some embodiments, the primer sequence may further include at least a portion of the oligonucleotide adaptor and a 5' tail oligonucleotide sequence.

In some embodiments, the second probe may further include a 5' tail oligonucleotide sequence.

In some embodiments, the DNA sample may be fragmented, thereby generating the double-stranded DNA fragment including the nucleic acid sequence of interest. An oligonucleotide adaptor may be ligated to each 5' end of the double-stranded DNA fragment, and the oligonucleotide adaptor may include a priming site, a barcode, and a variable sequence or a random sequence. The 3' ends of the double-stranded DNA fragment may be extended with a DNA polymerase using two strands of the double-stranded DNA fragment as a template, respectively. In some embodiments, the barcode may include an oligonucleotide sequence capable of identifying the DNA sample. In some embodiments, the variable sequence may include an oligonucleotide sequence capable of marking duplicate sequencing reads. In some instances, a first oligonucleotide adaptor may be ligated to the 5' end of a first strand of the double-stranded DNA fragment, and the first oligonucleotide adaptor may include an index priming site, a first barcode, and a first variable sequence. A second oligonucleotide adaptor may be ligated to the 5' end of a second strand of the double-stranded DNA fragment, and the second oligonucleotide adaptor may include the index priming site, a second barcode, and a second variable sequence. For example, the first barcode and the second barcode are identical. In some embodiments, the first oligonucleotide adaptor may further include a forward sequencing primer sequence, and the second oligonucleotide adaptor may further include the forward sequencing primer sequence.

Figure 2:
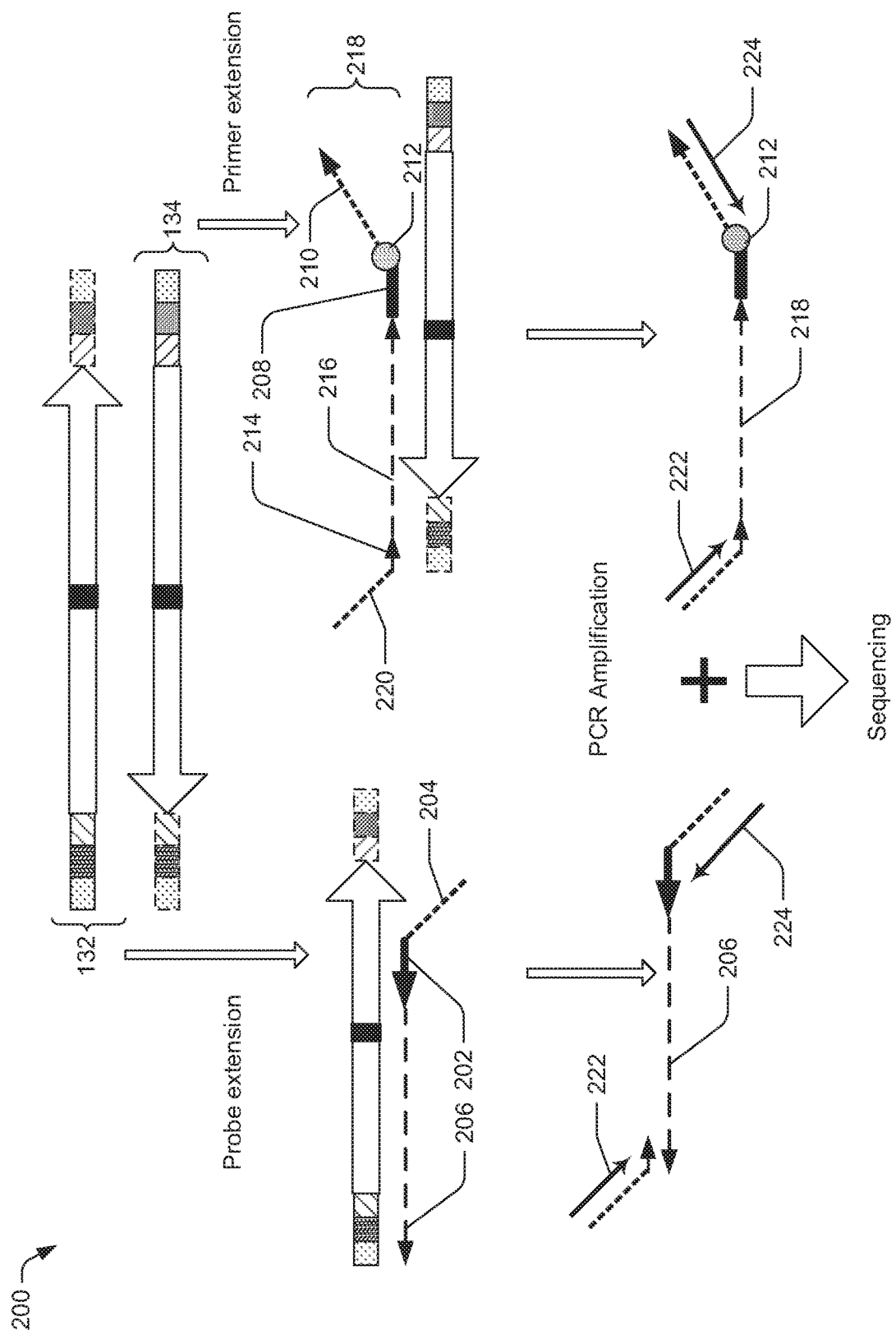
FIG. 2 is a diagram illustrating an exemplary process to distinguish a false positive from a true positive modification in nucleic acid sequencing.
Figure 3:
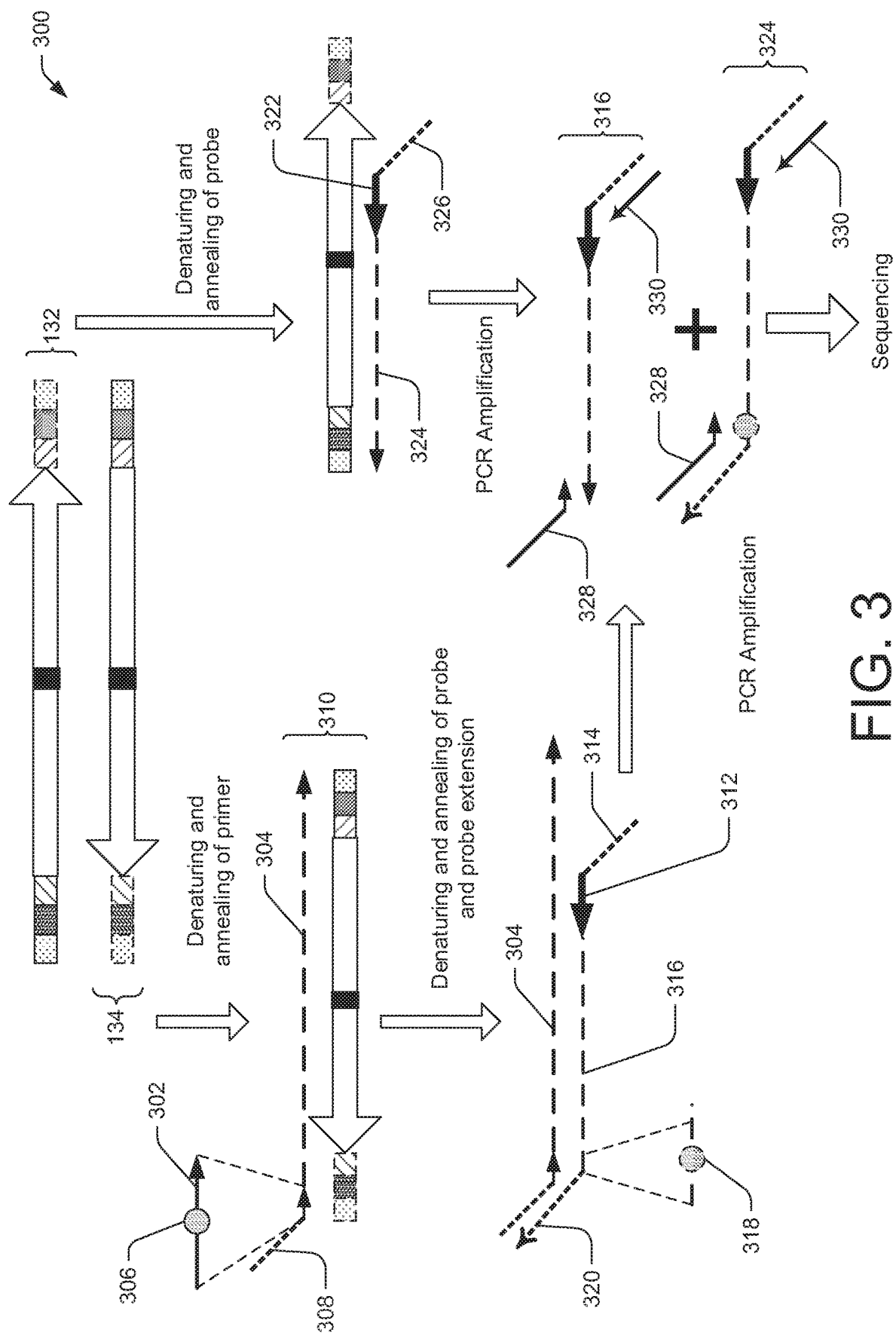
FIG. 3 is a diagram illustrating an exemplary process to distinguish a false positive from a true positive modification in nucleic acid sequencing.

Processes for determining a modification of one or more nucleotides during processing of nucleic acid samples are illustrated in FIG. 1, FIG. 2 and FIG. 3. In some embodiments, the modification may include a SNV, which may be a false positive or a true positive. For example, the modification may occur in one strand (e.g., dC to dU via oxidation) and therefore result in an error in sequence determination of the strand. In these instances, the complementary strand still has a dG in the related location. This inconsistency may be identified by sequencing both strands and therefore mark the error as a false positive.

The numbering scheme used in the figures is illustrative only. The same number appearing in more than one figure is not all intended to indicate an identical oligonucleotide sequence, in whole or in part but rather a component, site or region of reference for practicing the disclosed methods.

FIG. 1 is a diagram illustrating an exemplary process 100 to generate a nucleic acid fragment linked with one or more adaptors. A nucleic acid fragment (e.g., a DNA fragment 102) may be generated by fragmenting a nucleic acid sample. In certain example, the nucleic acid sample may include nucleic acid molecules from FFPE or plasma samples, which may be partially degraded and have base modifications (oxidation, etc.).

As illustrated in FIG. 1, the DNA fragment 102 is a double-stranded DNA fragment, which includes a strand 104 and a strand 106. The DNA fragment 102 has a nucleotide sequence of interest 108 in the strand 104 and its complement 110 in the strand 106. Adaptors 112 and 114 may be ligated to 5' ends of the strand 104 and the strand 106, respectively.

The adaptor 112 may include at least one of an oligonucleotide sequence 116, an oligonucleotide sequence 118, and an oligonucleotide sequence 120. In some embodiments, the oligonucleotide sequence 116 may include an index priming site, which is complementary to a forward primer for PCR amplification. The oligonucleotide sequence 118 may include a barcode and/or variable sequence. The barcode is used to identify the DNA sample and the variable sequence is used in marking duplicate sequencing reads. The oligonucleotide sequence 120 may include a forward sequencing primer sequence.

Similarly, the adaptor 114 may include at least one of an oligonucleotide sequence 122, an oligonucleotide sequence 124, and an oligonucleotide sequence 126. In some embodiments, the oligonucleotide sequence 122 may include an index priming site, which is complementary to a forward primer for PCR amplification. The oligonucleotide sequence 124 may include a barcode and/or variable sequence. The oligonucleotide sequence 126 may include a forward sequencing primer sequence.

In certain embodiments, the oligonucleotide sequences 116 and 122 are identical and the oligonucleotide sequences 120 and 126 are identical, while the oligonucleotide sequences 118 and 124 are not identical. In other embodiments, the oligonucleotide sequences 116 and 122 are identical, the oligonucleotide sequences 120 and 126 are identical, and the oligonucleotide sequences 118 and 124 are at least partially identical. For example, barcodes of the oligonucleotide sequences 118 and 124 are identical. In some instances, variable sequences of the oligonucleotide sequences 118 and 124 are not identical.

Upon ligation of the adaptors 112 and 114, the 3' ends of the strand 104 and the strand 106 may be extended with a DNA polymerase using each other as templates, thereby generating a double strand DNA fragment linked with a pair of adaptors on 3' ends and 5' ends. For example, the strand 104 has the adaptor 112 on 5' end and the complement 128 of the adaptor 114 on 3' end, and the strand 106 has the adaptor 114 on 5' end and the complement 130 of the adaptor 112 on 3' end. As illustrated in FIG. 1, the resulting DNA fragment 136 has two extended single strands: a strand 132 and a strand 134.

FIG. 2 is a diagram illustrating an exemplary process 200 to distinguish a false positive from a true positive in nucleic acid sequencing. The DNA fragment 136 may be denatured to generate the strand 132 and the strand 134. A probe may be annealed to the strand 132. The probe may include a probe oligonucleotide sequence 202, which is complementary to and hybridizes to a probe target region. The probe target region is located on the strand 132 and is associated with the nucleotide sequence of interest 108. For example, the probe target region is located at a downstream site of the nucleotide sequence of interest 108. The probe may be extended with a DNA polymerase using the strand 132 as a template and therefore form a probe extension sequence 206. In some embodiments, the probe may further include a 5' end linker oligonucleotide 204, which may include a common sequence for amplification and/or sequencing.

Another probe may be annealed to the strand 134. The probe may include a non-extendable probe 208, which is complementary to and hybridizes to a probe target region. The probe target region is located on the strand 134 and is associated with the nucleotide sequence of interest 110. For example, the probe target region is located at an upstream site of the nucleotide sequence of interest 110. In some embodiments, the probe may further include a 3' end linker oligonucleotide 210, which may include a common sequence for amplification and/or sequencing. In certain embodiments, the probe may further include a tag sequence 212, which is located between the non-extendable probe 208 and 3' end linker oligonucleotide 210.

Further, a primer 214 may be annealed to the strand 134. The primer 214 may be then extended with a DNA polymerase using the strand 134 as a template to form an extended primer sequence 216. The extended primer sequence 216 may be ligated to the non-extendable probe 208 and therefore form a primer extension sequence 218. In some embodiments, the primer 214 may be attached with a 5' end linker oligonucleotide sequence 220, which may include a common sequence for amplification and/or sequencing.

The probe extension sequence 206 and primer extension sequence 218 may be amplified using PCR primers. For example, a PCR primer with forward flowcell sequence 222 and a PCR primer with reverse flowcell sequence 224 may be used to amplify the probe extension sequence 206 and the primer extension sequence 218. The resulting DNA fragments may be sequenced. Because of the tag sequence 212, the sequencing results originating from the strand 104 and the strand 106 may be distinguishable. Accordingly, a true or false positive (e.g., a SNV) may be distinguished by comparing the sequencing results of the strand 104 and the strand 106.

FIG. 3 is a diagram illustrating another exemplary process 300 to distinguish a false positive from a true positive in nucleic acid sequencing. The DNA fragment 136 may be denatured and therefore two strands (i.e., the strand 132 and the strand 134) are generated. A primer 302 may be annealed to the strand 134 and the strand 132. The primer 302 may be extended with a DNA polymerase using the strand 134 as a template to form a primer extension sequence 304 and therefore generate a double-stranded DNA sequence 310. The primer 302 may include a tag sequence 306 and linked to a 5' end linker oligonucleotide 308, which may include a common sequence for amplification and/or sequencing.

The double-stranded DNA sequence 310 may be denatured, and a first probe may be annealed to the primer extension sequence 304. The first probe may include a probe oligonucleotide sequence 312, which is complementary to and hybridizes to the complement of a probe target region. The probe target region is located on the strand 134 and is associated with the nucleotide sequence of interest 110. For example, the probe target region is located at an upstream site of the nucleotide sequence of interest 110. In some embodiments, the first probe may further include a 5' end linker oligonucleotide 314, which may include a common sequence for amplification and/or sequencing.

The first probe may be extended with a DNA polymerase using the primer extension sequence 304 as a template and therefore generate a probe extension sequence 316, which includes a tag sequence 318 complementary to the tag sequence 306. The probe extension sequence 316 may further include a 3' end linker oligonucleotide 320, which may include a common sequence for amplification and/or sequencing.

Upon denaturing of the DNA fragment 136, a second probe may be annealed to the strand 132. The second probe may include an oligonucleotide sequence 322, which is complementary to and hybridizes to a probe target region. The probe target region is located on the strand 132 and is associated with the nucleotide sequence of interest 108. For example, the probe target region is located at a download site of the nucleotide sequence of interest 108. The second probe may be extended with a DNA polymerase using the strand 132 as a template and therefore generate a probe extension sequence 324. In some embodiments, the second probe may further include a 5' end linker oligonucleotide 326, which may include a common sequence for amplification and/or sequencing. In certain embodiments, the oligonucleotide sequences 312 and 322 are identical. In certain embodiments, 5' end linker oligonucleotides 314 and 326 are identical. In some instances, the first probe and the second probe are identical.

The probe extension sequence 316 and probe extension sequence 324 may be amplified using PCR primers. For example, a PCR primer with forward flowcell sequence 328 and a PCR primer with reverse flowcell sequence 330 may be used to amplify the probe extension sequence 316 and the probe extension sequence 324. The resulting DNA fragments may be sequenced. Because of the tag sequences 306 and 318, the sequencing results originating from the strand 104 and the strand 106 may be distinguishable. Accordingly, a true and false positive (e.g., a SNV) may be distinguished by comparing the sequencing results of the strand 104 and the strand 106.

The methods of the present disclosure can be used in the analysis of genetic information of selective genomic regions of interest as well as genomic regions that can interact with the selective region of interest. Amplification methods as disclosed herein can be used in the devices, kits, and methods known to the art for genetic analysis. In some cases, amplification methods of the present disclosure can be used to amplify target nucleic acid of interest for DNA hybridization studies to determine the presence or absence of polymorphisms. The polymorphisms, or alleles, can be associated with diseases or conditions such as genetic disease. In other case the polymorphisms can be associated with susceptibility to diseases or conditions, for example, polymorphisms associated with addiction, degenerative and age related conditions, cancer, and the like. In other cases, the polymorphisms can be associated with beneficial traits such as increased coronary health, or resistance to diseases such as HIV or malaria, or resistance to degenerative diseases such as osteoporosis, Alzheimer's or dementia.

The methods of the present disclosure can be used in the digital analysis of gene expression, gene expression patterns associated with disease, including diagnosis, prognosis and detection as well as identifying genetic disorders, e.g., chromosomal or gene translocations, deletions, duplications and defects as well as studying selective genomic regions of interest and genomic regions that can interact with the selective region of interest. In some embodiments, determination of Digital Gene Expression (DGE) or Copy Number Variation (CNV) digital measurements can be achieved by quantitating the number of gene reads within the total number of reads. In some embodiments, paired end sequencing can be performed. Sequencing can be performed via high throughput sequencing on a variety of platforms as is known to one of skill in the art. In some embodiments, the sequencing data/reads are mapped to the genome/transcriptome (for cDNA).

Any of the compositions described herein can be included in a kit. In a non-limiting example, the kit, in suitable container means, may include: one adaptor with a known sequence, one probe having a sequence specific portion and common portion of known sequence, one forward primer having a direct partial complement to the at least either the adaptor or probe common portion and one reverse primer having a direct partial complement to either the adaptor or probe common portion. The kit can further contain additional adaptors, primers and/or reagents useful for ligation, target enrichment and library preparation. The kit can further optionally contain a DNA-polymerase. The kit can further optionally contain reagents for amplification, for example reagents useful for PCR amplification methods. The kit can further optionally contain reagents for sequencing, for example, reagents useful for next-generation massively parallel sequencing methods.

The containers of the kits can include at least one vial, test tube, flask, bottle, syringe or other containers, into which a component can be placed, and preferably, suitably aliquoted. Where there is more than one component in the kit, the kit also can contain a second, third or other additional container into which the additional components can be separately placed. However, various combinations of components can be included in a container.

When the components of the kit can be provided in one or more liquid solutions, the liquid solution can be an aqueous solution. However, the components of the kit can be provided as dried powder(s). When reagents and/or components are provided as a dry powder, the powder can be reconstituted by the addition of a suitable solvent.

A kit can include instructions for employing the kit components as well the use of any other reagent not included in the kit. Instructions can include variations that can be implemented.

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

What is claimed is:

1. A method of identifying a false positive modification in nucleic acid sequencing of a DNA sample, the method comprising:
    preparing a double-stranded DNA fragment linked with a plurality of oligonucleotide adaptors, the double-stranded DNA fragment comprising a nucleic acid sequence of interest;
    denaturing the double-stranded DNA fragment, thereby generating a first strand DNA fragment and a second strand DNA fragment;
    annealing a first probe to the first strand DNA fragment, the first probe comprising a probe oligonucleotide sequence complementary to and hybridizing to a first probe target region associated with the nucleic acid sequence of interest;
    extending the first probe with a DNA polymerase using the first strand DNA fragment as a template, thereby generating a probe extension sequence;
    annealing a second probe to the second strand DNA fragment, the second probe comprising a non-extendable probe sequence and a tag sequence, the non-extendable probe sequence complementary to and hybridizing to a second probe target region associated with the nucleic acid sequence of interest;
    annealing a primer sequence to the 3' end of the second strand DNA fragment;
    extending the primer sequence with the DNA polymerase using the second strand DNA fragment as a template, thereby generating a primer extension sequence;
    ligating the primer extension sequence and the second probe thereby generating a ligated primer extension sequence comprising the tag sequence; and
    sequencing the ligated primer extension sequence and the probe extension sequence, thereby identifying a false positive modification in the nucleic acid sequencing.

2. The method of claim 1, wherein the false positive modification comprises a false positive single nucleotide polymorphism (SNP).

3. The method of claim 1, wherein the DNA sample comprises a DNA sample derived from a FFPE material or plasma.

4. The method of claim 1, further comprising:
amplifying the probe extension sequence and the ligated primer extension sequence using PCR primers.

5. The method of claim 1, wherein the second probe further comprises a 3' tail oligonucleotide sequence, and the primer sequence further comprises a 5' tail oligonucleotide sequence for amplification.

6. The method of claim 5, wherein the amplifying the probe extension sequence and the ligated primer extension sequence using PCR primers comprises:
amplifying the ligated primer extension sequence using a first primer that is directed against the complement of at least a portion of an oligonucleotide adaptor of the plurality of oligonucleotide adaptors and a second primer that is directed against at least a portion of the 5' tail oligonucleotide sequence; and
amplifying the probe extension sequence using a third primer.

7. The method of claim 6, wherein the sequencing the ligated primer extension sequence and the probe extension sequence, thereby the false positive modification in the nucleic acid sequencing comprises:
sequencing the probe extension sequence and the ligated primer extension sequence thereby generating a sequencing result;
collecting first sequencing information of the nucleic acid sequence of interest associated with the first strand DNA fragment and second sequencing information of the nucleic acid sequence of interest associated with the second strand DNA fragment based on the sequencing result; and
the false positive modification in the nucleic acid sequencing by comparing the first sequencing information and the second sequencing information.

8. The method of claim 1, wherein the preparing a double-stranded DNA fragment linked with the plurality of oligonucleotide adaptors comprises:
fragmenting the DNA sample, thereby generating the double-stranded DNA fragment comprising the nucleic acid sequence of interest;
ligating an oligonucleotide adaptor to each 5' end of the double-stranded DNA fragment, the oligonucleotide adaptor comprising a priming site, a barcode, and a variable sequence; and
extending 3' ends of the double-stranded DNA fragment with a DNA polymerase using two strands of the double-stranded DNA fragment as a template, respectively.

9. The method of claim 8, wherein the barcode comprises an oligonucleotide sequence capable of identifying the DNA sample.

10. The method of claim 8, wherein the variable sequence comprises an oligonucleotide capable of marking duplicate sequencing reads.

11. The method of claim 8, wherein the ligating an oligonucleotide adaptor to each 5' end of the double-stranded DNA fragment comprises:
ligating a first oligonucleotide adaptor to the 5' end of a first strand of the double-stranded DNA fragment, the first oligonucleotide adaptor comprising an index priming site, a first barcode, and a first variable sequence; and
ligating a second oligonucleotide adaptor to the 5' end of a second strand of the double-stranded DNA fragment, the second oligonucleotide adaptor comprising the index priming site, a second barcode, and a second variable sequence.

12. The method of claim 11, wherein the first barcode and the second barcode are identical.

13. The method of claim 11, wherein the first oligonucleotide adaptor further comprises a forward sequencing primer sequence, and the second oligonucleotide adaptor further comprises a forward sequencing primer sequence.

14. A method of identifying a false positive modification in nucleic acid sequencing of a DNA sample, the method comprising:
preparing a double-stranded DNA fragment linked with a plurality of oligonucleotide adaptors, the double-stranded DNA fragment comprising a nucleic acid sequence of interest;
denaturing the double-stranded DNA fragment, thereby generating a first strand DNA fragment and a second strand DNA fragment;
annealing a first probe to the first strand DNA fragment, the first probe comprising a probe oligonucleotide sequence complementary to and hybridizing to a first probe target region associated with the nucleic acid sequence of interest;
extending the first probe with a DNA polymerase using the first strand DNA fragment as a template, thereby generating a probe extension sequence;
annealing a primer sequence to the second strand DNA fragment, the primer sequence comprising a tag sequence;
extending the primer sequence with a DNA polymerase using the second strand DNA fragment as a template thereby generating a primer extension sequence;
denaturing the primer extension sequence and the second strand DNA fragment;
annealing a second probe to the primer extension sequence, the second probe comprising a second probe oligonucleotide sequence complementary to and hybridizing to a second probe target region associated with the nucleic acid sequence of interest;
extending the second probe annealed to the primer extension sequence with the DNA polymerase using the primer extension sequence as a template, thereby generating an additional probe extension sequence comprising a sequence complementary to the tag sequence; and
sequencing the probe extension sequence and the additional probe extension sequence, thereby identifying the false positive modification in the nucleic acid sequencing.

15. The method of claim 14, wherein the primer sequence further comprises at least a portion of the oligonucleotide adaptor and a 5' tail oligonucleotide sequence.

16. The method of claim 14, wherein the second probe further comprises a 5' tail oligonucleotide sequence.

17. The method of claim 14, wherein the false positive modification comprises a false positive single nucleotide polymorphism (SNP).

18. The method of claim 14, wherein the DNA sample comprises a DNA sample derived from a FFPE material or plasma.

19. The method of claim 14, wherein the preparing a double-stranded DNA fragment linked with the plurality of oligonucleotide adaptors comprises:
fragmenting the DNA sample, thereby generating the double-stranded DNA fragment comprising the nucleic acid sequence of interest;

ligating an oligonucleotide adaptor to each 5' end of the double-stranded DNA fragment, the oligonucleotide adaptor comprising a priming site, a barcode, and a variable sequence; and extending 3' ends of the double-stranded DNA fragment with a DNA polymerase using two strands of the double-stranded DNA fragment as a template, respectively.

20. The method of claim 19, wherein the barcode comprises an oligonucleotide sequence capable of identifying the DNA sample.

21. The method of claim 19, wherein the variable sequence comprises an oligonucleotide capable of marking duplicate sequencing reads.

22. The method of claim 19, wherein the ligating an oligonucleotide adaptor to each 5' end of the double-stranded DNA fragment comprises:

ligating a first oligonucleotide adaptor to the 5' end of a first strand of the double-stranded DNA fragment, the first oligonucleotide adaptor comprising an index priming site, a first barcode, and a first variable sequence; and ligating a second oligonucleotide adaptor to the 5' end of a second strand of the double-stranded DNA fragment, the second oligonucleotide adaptor comprising the index priming site, a second barcode, and a second variable sequence.

23. The method of claim 22, wherein the first barcode and the second barcode are identical.

24. The method of claim 22, wherein the first oligonucleotide adaptor further comprises a forward sequencing primer sequence, and the second oligonucleotide adaptor further comprises a forward sequencing primer sequence.

* * * * *